United States Patent
Husain

(10) Patent No.: US 6,242,655 B1
(45) Date of Patent: Jun. 5, 2001

(54) GLYCOL PURIFICATION

(75) Inventor: Mansoor Husain, Berkeley Heights, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 09/613,395

(22) Filed: Jul. 11, 2000

(51) Int. Cl.[7] .................................................... C07C 27/26
(52) U.S. Cl. ...................... 568/872; 568/868; 568/867; 568/852
(58) Field of Search ................................. 568/870, 868, 568/869, 852, 872, 867

(56) References Cited

U.S. PATENT DOCUMENTS 3,732,320 * 5/1973 Ford ............................. 260/637 R
4,349,417 * 9/1982 Rebsdat et al. ........................ 203/33
4,358,625 * 11/1982 Paggini et al. ........................ 568/867
5,294,305 * 3/1994 Craft, Sr. et al. ....................... 203/28

FOREIGN PATENT DOCUMENTS

2558039 A1 * 12/1975 (DE).

* cited by examiner

Primary Examiner—Johann Richter
Assistant Examiner—Elvis O. Price
(74) Attorney, Agent, or Firm—William C. Long

(57) ABSTRACT

High purity ethylene glycol containing 2000 ppm or less aldehyde is contacted with a solid strong acid cation exchange resin and an ethylene glycol product reduced in aldehydes content is recovered.

5 Claims, No Drawings

GLYCOL PURIFICATION

BACKGROUND OF THE INVENTION

1. Field of the Invention

The present invention relates to the preparation of ethylene glycol having reduced aldehyde impurities content and improved ultraviolet transmission characteristics by treatment of already high purity distilled ethylene glycol (99% or higher) with strong acid cation exchange resin.

2. Description of the Prior Art

Ethylene glycol is a very important chemical of commerce which is usually prepared by reaction of ethylene oxide and water. A problem which has existed is that during the preparation procedure impurities such as aldehydes are formed which are difficult to separate from ethylene glycol and which cause problems in applications where very high purity is required, for example in the manufacture of fibers.

Both physical methods as well as chemical methods have been devised for the separation of aldehydes from ethylene glycol. U.S. Pat. No. 4,349,417, for example, proposes distillation in the presence of a alkali metal compounds as a purification procedure. This patent also refers to German Ausligeschrift No. 2,558,039 as teaching ethylene glycol purification using an ion exchange resin.

This German reference in turn refers to Wertschaft patent no. 43911 which teaches that aliphatic alcohols which contain more than 2% formaldehyde can be purified by converting the formaldehyde to formal using an acid catalyst followed by distillation of the impure, formal-containing alcohol. The patent states that at formaldehyde contents of less than 2% the amount of formaldehyde which is converted to the corresponding formal is so small that it is no longer possible to conduct the workup economically. Acid form ion-exchange resins are taught as suitable catalysts.

U.S. Pat. No. 4,358,625 teaches reducing oxygen-containing impurities by treatment with alkali metal borohydride.

U.S. Pat. No. 3,904,656 teaches treating a purge stream from an ethylene oxide stripper with a cation exchange resin Amberlyst A-15, an anion exchange resin Amberlyst A-21, and a carbon bed prior to recycle.

U.S. Pat. No. 4,560,813 teaches hydrolysis of alkylene oxide using a methylate anion—containing natural and recovery of the methylate anion by contact with a solid such as anion exchange resin.

U.S. Pat. No. 5,440,058 mentions treatment of aqueous streams with weakly basic ion exchange resins which have been reacted with a bisulfite salt in order to remove aldehyde impurities.

Despite the efforts of prior workers, further improvements in the removal of impurities such as aldehydes from aqueous ethylene glycol streams is important and desirable.

The presence of even very small amounts of aldehyde impurities ie. 2000 ppm by weight or less, has a deleterious effect on the properties of ethylene glycol and it is very important that economic procedures be provided to remove these materials or to convert them to a non-harmful form.

BRIEF DESCRIPTION OF THE INVENTION

In accordance with the invention, a distilled ethylene glycol stream which contains very small amounts aldehyde impurities is contacted with a strong acid cation exchange resin which had been pretreated to remove leachables and a resulting ethylene glycol stream greatly reduced in aldehydes content and having improved ultraviolet transmission is recovered.

DETAILED DESCRIPTION

Strong acid cation exchange resins are used in the process of the invention.

Cation exchange resins containing sulfonic acid functional groups are especially preferred, such as styrene-divingl benzene polymers with sulfonic acid groups. Tulison PTR is illustrative. It is important that the strong acid resin be pretreated, preferably by a hot water followed by vacuum drying pretreatment, until substantially all of the leachable impurities associated with the resin are removed. If this is not done, although the resin is still useful for reduction of aldehyde content actually the ultraviolet transmission characteristics of the treated ethylene glycol is adversely affected.

Ethylene glycol which is purified in accordance with the invention is a distillate derived from ethylene oxide by conventional procedures and contains about 2000 ppm or less of total aldehydes, preferably 5 to 100 ppm aldehydes. Generally the ethylene glycol to be treated contains at most minor amounts of water, 0–1% by weight. Small amounts of unsaturated organic materials may also be present in the glycol to be treated.

The ethylene glycol solution is contacted with the solid strong acid resin at moderate temperatures, eg. about 30 to 50° C. although temperatures outside this range can be used. Atmospheric pressure is preferred but higher pressures can be used. Illustrative flow rates are about 1 to 10 volumes of solution per volume of resin per hour although this can vary widely.

Ion exchange resins which are employed in practice of the invention are strongly acidic cation exchange resins which are well known articles of commerce.

A comprehensive description of strong acid exchange resin suitable for use herein and their preparation can be found in Kirk-Othmer, Encyclopedia of Chemical Technology, 5th Edition, Vol 14 pages 747–749 (1990).

The following examples illustrate the invention:

An ethylene glycol stream comprised of 99.8% by weight ethylene glycol, 0.05 weight % water, and 20 ppm aldehydes (mainly formaldehyde) was passed through a bed of particulate strongly acidic macroporous styrene-divinyl benzene resin with sulfonic acid groups (Tulison PTR) at 35° C. The resin had been pretreated by hot water washing and vacuum drying until essentially all of the leachable impurities had been removed. After 5 volumes of ethylene glycol feed were treated by the resin per volume of resin, the outlet solution aldehyde concentration was below 2 ppm.

The above example was repeated using a monoethylene glycol process stream comprised of 99.9 wt % monoethylene glycol, 0.02% wt % water and containing 10 ppm of aldehyde. As a result of the contact the total aldehydes content was reduced to 1 ppm in the effluent stream.

In addition to the efficient reduction in aldehyde content achieved in accordance with practice of the invention, an additional noteworthy result was an improvement in ultraviolet transmission of from 93% (untreated glycol) to 96% transmission at a wavelength of 220 nm for the treated glycol and from 92% to (untreated) to 97% transmission at a wavelength of 275 nm for the glycol treated according to the invention.

We claim:

1. The method for reducing the aldehyde content of ethylene glycol containing 2000 ppm or less of aldehyde which comprises contacting the glycol in liquid phase with a solid strong acid cation exchange resin.

2. The method of claim 1 wherein the aldehyde content of the ethylene glycol treated is 5 to 100 ppm.

3. The method of claim 1 where the solid strong acid cation exchange resin comprises sulfonic acid group.

4. The method of claim 1 wherein the glycol has a water content of 0–1 wt %.

5. The method of claim 1 wherein the strong acid cation exchange resin has been pretreated to remove substantially all for the leachable impurities therefrom prior to contact with the ethylene glycol.

* * * * *